US00PP35549P3

(12) United States Plant Patent
Barends

(10) Patent No.: US PP35,549 P3
(45) Date of Patent: Dec. 12, 2023

(54) ***PERICALLIS* PLANT NAMED 'DOMAPLUROBL'**

(50) Latin Name: ***Pericallis* x *hybrida***
Varietal Denomination: Domaplurobl

(71) Applicant: DUMMEN GROUP B.V., De Lier (NL)

(72) Inventor: Eveline Desiree Barends, De Lier (NL)

(73) Assignee: DUMMEN GROUP B.V., De Lier (NL)

( * ) Notice: Subject to any disclaimer, the term of this patent is extended or adjusted under 35 U.S.C. 154(b) by 0 days.

(21) Appl. No.: 18/075,956

(22) Filed: Dec. 6, 2022

(65) Prior Publication Data

US 2023/0180645 P1 Jun. 8, 2023

(30) Foreign Application Priority Data

Dec. 8, 2021 (QZ) ..... PBR 2021/3203

(51) Int. Cl.
*A01H 6/14* (2018.01)
*A01H 6/80* (2018.01)

(52) U.S. Cl.
USPC ..... Plt./263.1
CPC ..... *A01H 6/80* (2018.05)

(58) Field of Classification Search
USPC ..... Plt./263.1
CPC ..... A01H 6/14; A01H 5/02
See application file for complete search history.

(56) References Cited

PUBLICATIONS

CPVO Register (Year: 2023).*

* cited by examiner

*Primary Examiner* — Keith O. Robinson
(74) *Attorney, Agent, or Firm* — C. Anne Whealy

(57) ABSTRACT

A new and distinct cultivar of *Pericallis* plant named 'Domaplurobl', characterized by its broadly upright and mounded plant habit; freely branching growth habit; dark green-colored leaves; freely flowering habit; and medium-sized daisy-type inflorescences with dark purple-colored ray florets.

1 Drawing Sheet

Botanical designation: *Pericallis* x *hybrida.*
Cultivar denomination: 'DOMAPLUROBL'.

CROSS REFERENCED TO CLOSELY-RELATED APPLICATION

An European Community Plant Breeder's Rights application for the instant plant was filed by the Applicant/Assignee, Dümmen Group B.V. of De Lier, The Netherlands on Dec. 8, 2021, application number 2021/3203 and published on Feb. 15, 2022.

Foreign priority is claimed to this application.

BACKGROUND OF THE INVENTION

The present invention relates to a new and distinct cultivar of *Pericallis* plant, botanically known as *Pericallis* x *hybrida* and hereinafter referred to by the name 'Domaplurobl'.

The new *Pericallis* plant is a product of a planned breeding program conducted by the Inventor in De Lier, The Netherlands. The objective of the breeding program is to create new vigorous and freely-branching *Pericallis* plants with numerous attractive medium-sized inflorescences.

The new *Pericallis* plant originated from a cross-pollination made by the Inventor in February, 2017 in De Lier, The Netherlands of a proprietary selection of *Pericallis* x *hybrida* identified as code number SN-0295, not patented, as the female, or seed, parent with a proprietary selection of *Pericallis* x *hybrida* identified as code number SN-0523, not patented, as the male, or pollen, parent. The new *Pericallis* plant was discovered and selected by the Inventor as a single flowering plant from within the progeny of the stated cross-pollination in a controlled greenhouse environment in De Lier, The Netherlands in February, 2018.

Asexual reproduction of the new *Pericallis* plant by vegetative terminal cuttings in a controlled greenhouse environment in De Lier, The Netherlands since March, 2018 has shown that the unique features of this new *Pericallis* plant are stable and reproduced true to type in successive generations.

SUMMARY OF THE INVENTION

Plants of the new *Pericallis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Domaplurobl'. These characteristics in combination distinguish 'Domaplurobl' as a new and distinct *Pericallis* plant:

1. Broadly upright and mounded plant habit.
2. Freely branching growth habit.

3. Dark green-colored leaves.
4. Freely flowering habit.
5. Medium-sized daisy-type inflorescences with dark purple-colored ray florets.

Plants of the new *Pericallis* differ from plants of the female parent selection primarily in plant habit as plants of the new *Pericallis* are more vigorous than and not as compact as plants of the female parent selection.

Plants of the new *Pericallis* differ from plants of the male parent selection primarily in ray floret color as ray florets of plants of the new *Pericallis* are dark purple in color whereas ray florets of plants of the male parent selection are violet and white bi-colored.

Plants of the new *Pericallis* can be compared to plants of *Senecio cruentus* 'Sunsenedibu', disclosed in U.S. Plant Pat. No. 12,181. In side-by-side comparisons, plants of the new *Pericallis* differ from plants of 'Sunsenedibu' in the following characteristics:

1. Lateral branches of plants of the new *Pericallis* are dark purple in color whereas lateral branches of plants of 'Sunsenedibu' are medium green in color.
2. Plants of the new *Pericallis* have darker green-colored leaves than plants of 'Sunsenedibu'.
3. Plants of the new *Pericallis* are more freely flowering than plants of 'Sunsenedibu'.
4. Plants of the new *Pericallis* have larger inflorescences than plants of 'Sunsenedibu'.
5. Ray florets of plants of the new *Pericallis* are broader and more imbricate than ray florets of plants of 'Sunsenedibu'.

BRIEF DESCRIPTION OF THE PHOTOGRAPH

The accompanying photograph illustrates the overall appearance of the new *Pericallis* plant showing the colors as true as it is reasonably possible to obtain in colored reproductions of this type. Colors in the photograph may differ slightly from the color values cited in the detailed botanical description which accurately describe the colors of the new *Pericallis* plant.

The photograph is a side perspective view of a typical flowering plant of 'Domaplurobl' grown in a container.

DETAILED BOTANICAL DESCRIPTION

The aforementioned photograph, following observations and measurements describe plants grown during the spring in 12-cm containers in a glass-covered greenhouse in De Lier, The Netherlands and under cultural practices typically used in commercial *Pericallis* production. During the production of the plants, day temperatures ranged from 8° C. to 18° C. and night temperatures ranged from 6° C. to 16° C. Plants were 13 weeks old when the photograph was taken and were 17 weeks old when the description was taken. In the following description, color references are made to The Royal Horticultural Society Colour Chart, 2007 Edition, except where general terms of ordinary dictionary significance are used.

Botanical classification: *Pericallis* x *hybrida* 'Domaplurobl'.

Parentage:

*Female, or seed, parent*.—Proprietary selection of *Pericallis* x *hybrida* identified as code number SN-0295, not patented.

*Male, or pollen, parent*.—Proprietary selection of *Pericallis* x *hybrida* identified as code number SN-0523, not patented.

Propagation:

*Type*.—Terminal vegetative cuttings.

*Time to initiate roots, summer*.—About eight days at temperatures about 22° C. to 25° C.

*Time to initiate roots, winter*.—About ten days at temperatures about 18° C. to 20° C.

*Time to produce a rooted young plant, summer*.—About three weeks at temperatures about 22° C. to 25° C.

*Time to produce a rooted young plant, winter*.—About three weeks at temperatures about 18° C. to 20° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Not freely branching; medium density.

Plant description:

*Plant form and growth habit*.—Broadly upright and mounded plant habit; daisy-type inflorescences positioned above the foliar plane; freely branching habit with about eleven lateral branches developing per plant; dense and bushy appearance; moderately vigorous growth habit and moderate growth rate.

*Plant height, soil level to top of foliar plane*.—About 16 cm to 18 cm.

*Plant height, soil level to top of floral plane*.—About 26 cm to 28 cm.

*Plant diameter*.—About 37 cm to 39 cm.

*Lateral branches*.—Length: About 16 cm to 18 cm. Diameter: About 2 cm to 2.2 cm. Internode length: About 1 cm to 2 cm. Strength: Moderately strong. Aspect: Mostly upright. Texture and luster: Smooth, glabrous; semi-glossy. Color, developing and developed: Close to N187A.

*Leaf description*.—Arrangement: Alternate, simple. Length: About 8 cm to 10 cm. Width: About 9 cm to 11 cm. Shape: Deltoid. Apex: Acuminate. Base: Cordate. Margin: Incised; sinuses medium in depth and divergent. Texture and luster, upper surface: Smooth, glabrous; semi-glossy. Texture and luster, lower surface: Smooth, glabrous; matte. Venation pattern: Palmate. Color: Developing leaves, upper surface: Close to N137A to N137B. Developing leaves, lower surface: Close to N137B. Fully expanded leaves, upper surface: Close to N137A; venation, close to 137B. Fully expanded leaves, lower surface: Close to N137B; venation, close to N187A. Petioles: Length: About 4 cm to 5 cm. Diameter: About 3 mm to 5 mm. Strength: Moderately strong. Texture and luster, upper and lower surfaces: Smooth, glabrous; matte. Color, upper and lower surfaces: Close to N187A.

Inflorescence description:

*Appearance*.—Medium-sized daisy-type inflorescences with ligulate-shaped ray florets; inflorescences arising from upper leaf axils and positioned above the foliar plane; disc and ray florets developing acropetally on a capitulum; inflorescences face mostly upright; freely flowering habit with about 160 inflorescences developing per plant during the flowering season.

*Fragrance*.—None detected.

*Natural flowering season*.—In The Netherlands, plants of the new *Pericallis* flower continuously during the spring; plants begin flowering about six to eight weeks after planting depending on temperature.

*Inflorescence longevity*.—Inflorescences last about three to five days on the plant; inflorescences not persistent.

*Inflorescence buds*.—Height: About 5 mm to 6 mm. Diameter: About 1 mm to 2 mm. Shape: Ovoid. Texture and luster: Smooth, glabrous; semi-glossy. Color: Close to N187B.

*Inflorescence size*.—Diameter: About 5 cm to 7 cm. Depth (height): About 1 cm to 1.5 cm. Disc diameter: About 1 cm.

*Receptacles*.—Height: About 5 mm to 7 mm. Diameter: About 5 mm to 7 mm. Shape: Rounded. Color: Close to N187B.

*Ray florets*.—Quantity and arrangement: About ten to twelve per inflorescence arranged in a single whorl. Length: About 2 cm to 3 cm. Width: About 8 mm to 9 mm. Shape: Ligulate. Apex: Emarginate. Base: Obtuse. Margin: Entire; not undulate. Aspect: Initially upright to close to horizontal, flat. Texture and luster, upper surface: Smooth, glabrous; glossy. Texture and luster, lower surface: Smooth, glabrous; semi-glossy. Color: When opening, upper surface: Darker and more intense than 79A. When opening, lower surface: Close to 83A. Fully opened, upper surface: Darker and more intense than 79A; venation, darker and more intense than 79A; color becoming closer to 83A with subsequent development. Fully opened, lower surface: Close to 83A; venation, close to N87A; color does not change with subsequent development.

*Disc florets*.—Quantity and arrangement: About 90 to 100 per inflorescence arranged in about eight to nine whorls. Length: About 7 mm to 9 mm. Diameter: About 1 mm. Shape: Tubular; apex dentate, five-pointed. Texture and luster, inner and outer surfaces: Smooth, glabrous; matte. Color: When opening and fully opened, inner surface: Close to 191D; venation, close to 191D; color does not change with subsequent development. When opening and fully opened, outer surface: Close to 83A; venation, close to 83A; color becoming closer to 83B with subsequent development.

*Phyllaries*.—Quantity and arrangement: About 13 to 15 per inflorescence arranged in a single whorl. Length: About 5 mm to 7 mm. Width: About 1 mm to 2 mm. Shape: Lanceolate. Apex: Acute. Base: Cuneate. Margin: Entire. Texture and luster, upper and lower surfaces: Smooth, glabrous; matte. Color, upper surface: Close to 139B. Color, lower surface: Close to N189A.

*Peduncles*.—Length, terminal peduncle: About 4 cm to 5 cm. Length, third peduncle: About 5 cm to 6 cm. Diameter, terminal peduncle: About 1 mm. Diameter, third peduncle: About 1.5 mm. Strength: Strong. Aspect: Mostly upright. Texture and luster: Smooth, glabrous; semi-glossy. Color: Close to between N187A and N187B.

*Reproductive organs*.—Androecium: Present on disc florets only. Stamen quantity: One per disc floret. Filament length: About 1 mm to 2 mm. Filament color: Close to N89A. Anther size: About 1 mm by 3 mm. Anther shape: Oval. Anther color: Close to N89A. Pollen amount: Abundant. Pollen color: Close to 12A. Gynoecium: Present on both ray and disc florets. Pistil length: About 2 mm. Style length: About 1.5 mm. Style color: Close to N89B. Stigma shape: Crested. Stigma diameter: Less than 1 mm. Stigma color: Close to N92C.

*Seeds and fruits*.—To date, seed and fruit development has not been observed on plants of the new *Pericallis*.

Pathogen & pest resistance: To date, plants of the new *Pericallis* have not been observed to be resistant to pathogens and pests common to *Pericallis* plants.

Temperature tolerance: Plants of the new *Pericallis* have been observed to tolerate temperatures ranging from about 2° C. to about 30° C. and to be suitable for USDA Hardiness Zones 9a to 12b.

It is claimed:

1. A new and distinct *Pericallis* plant named 'Domaplurobl' as illustrated and described.

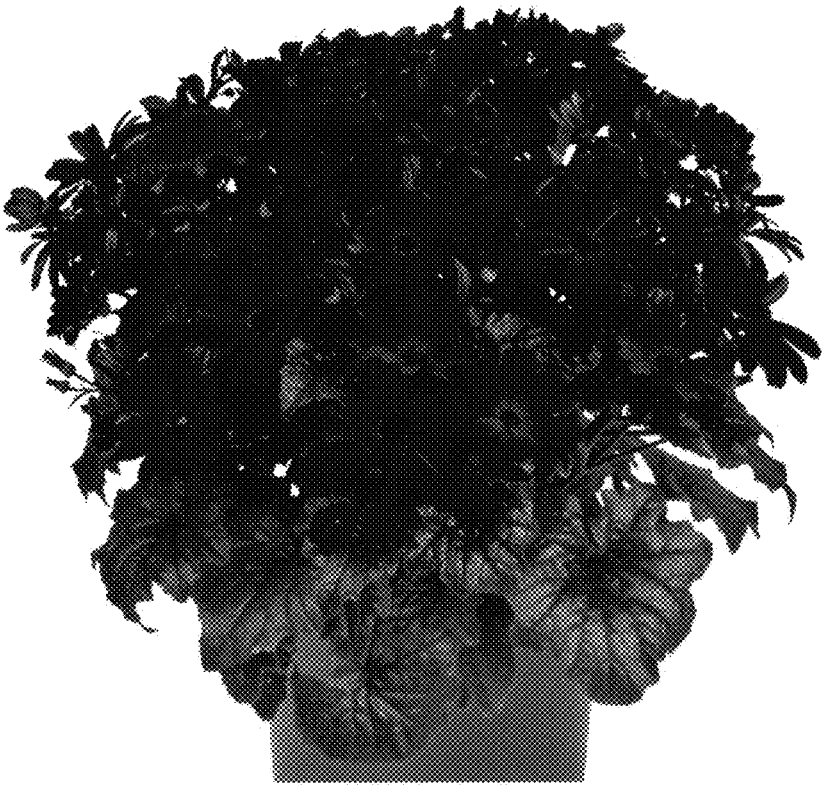

* * * * *